(12) United States Patent
Feldhues et al.

(10) Patent No.: US 9,637,619 B2
(45) Date of Patent: May 2, 2017

(54) POLYSULFIDE MIXTURES, METHOD FOR THE PRODUCTION THEREOF, AND USE OF THE POLYSULFIDE MIXTURES IN RUBBER MIXTURES

(71) Applicant: LANXESS Deutschland GmbH, Cologne (DE)

(72) Inventors: Ulrich Feldhues, Bergisch Gladbach (DE); Heinz Unterberg, Dormagen (DE); Hermann-Josef Weidenhaupt, Pulheim (DE); Melanie Wiedemeier-Jarad, Dormagen (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 14/434,892

(22) PCT Filed: Oct. 17, 2013

(86) PCT No.: PCT/EP2013/071688
§ 371 (c)(1),
(2) Date: Apr. 10, 2015

(87) PCT Pub. No.: WO2014/063983
PCT Pub. Date: May 1, 2014

(65) Prior Publication Data
US 2015/0284547 A1 Oct. 8, 2015

(30) Foreign Application Priority Data

Oct. 25, 2012 (EP) .................................... 12189995

(51) Int. Cl.
| C08L 9/06 | (2006.01) |
|---|---|
| B60C 1/00 | (2006.01) |
| C07C 323/52 | (2006.01) |
| C08K 5/372 | (2006.01) |
| C08L 21/00 | (2006.01) |
| C08G 75/14 | (2006.01) |
| C08J 3/24 | (2006.01) |
| C08K 5/548 | (2006.01) |

(52) U.S. Cl.
CPC ........ *C08L 9/06* (2013.01); *B60C 1/00* (2013.01); *C07C 323/52* (2013.01); *C08G 75/14* (2013.01); *C08J 3/247* (2013.01); *C08K 5/372* (2013.01); *C08K 5/548* (2013.01); *C08L 21/00* (2013.01); *C08J 2309/06* (2013.01); *C08J 2409/00* (2013.01); *C08J 2481/04* (2013.01); *C08L 2205/025* (2013.01); *C08L 2205/03* (2013.01)

(58) Field of Classification Search
CPC .. B60C 1/00; C08K 5/36; C08K 5/548; C08K 5/372; C08L 9/00; C08L 9/06; C08L 21/00; C08L 2205/02; C08L 2205/025; C07C 323/52; C08J 2309/06; C08J 2409/00; C08J 2481/04; C08J 3/247
See application file for complete search history.

(56) References Cited

U.S. PATENT DOCUMENTS

| 2,691,000 | A | * | 10/1954 | Scotchford | ............... C10M 1/08 |
|---|---|---|---|---|---|
| | | | | | 508/275 |
| 4,052,440 | A | * | 10/1977 | Gladstone | ............. C07C 323/00 |
| | | | | | 560/147 |
| 4,076,550 | A | | 2/1978 | Thurn et al. | |
| 4,709,065 | A | | 11/1987 | Yoshioka et al. | |
| 5,068,445 | A | * | 11/1991 | Arretz | ................... C07C 319/24 |
| | | | | | 560/147 |
| 5,663,226 | A | | 9/1997 | Scholl et al. | |
| 6,040,389 | A | * | 3/2000 | Wideman | ............... C07C 323/52 |
| | | | | | 524/262 |
| 6,268,421 | B1 | | 7/2001 | Dittrich et al. | |
| 9,023,926 | B2 | | 5/2015 | Wiedemeier et al. | |
| 2002/0014747 | A1 | | 2/2002 | Yamada et al. | |
| 2014/0155518 | A1 | | 6/2014 | Wiedemeier et al. | |

FOREIGN PATENT DOCUMENTS

EP 0489313 A1 6/1992

OTHER PUBLICATIONS

Arisawa et al., Rhodium-Catalyzed Sulfur Atom Exchange Reaction Between Organic Polysulfides and Sulfur, Tetrahedron Letters, 46 (2005) 4797-4800.
European Search Report for Appln EP 12189995, Jan. 28, 2013.

* cited by examiner

*Primary Examiner* — Satya Sastri

(57) ABSTRACT

The present invention relates to novel polysulfides mixtures comprising compounds of the formula (I)

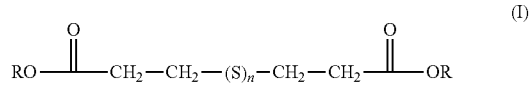

where n is from 2 to 6, and R is $C_1$-$C_8$-alkyl, to processes for the production of said polysulfides mixtures, to use of these for the production of rubber matures, and to rubber vulcanizates produced therefrom.

29 Claims, No Drawings

POLYSULFIDE MIXTURES, METHOD FOR THE PRODUCTION THEREOF, AND USE OF THE POLYSULFIDE MIXTURES IN RUBBER MIXTURES

The present invention relates to novel polysulfide mixtures, to processes for the production of said polysulfide mixtures, to the use of the polysulfide mixtures in rubber mixtures, to rubber vulcanizates produced therefrom, and to use of these.

Silica-containing rubber mixtures are important starting materials, for example for the production of tires with reduced rolling resistance. These consume less rolling deformation energy, and therefore reduce fuel consumption. Because various states have decided on compulsory marking to indicate rolling resistance on tires, there is a high level of interest in achieving a further reduction in this resistance.

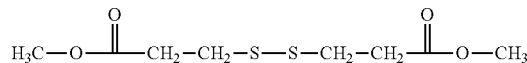
CAS: 15441-06-2

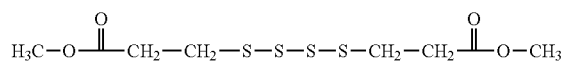
CAS: 862010-11-5

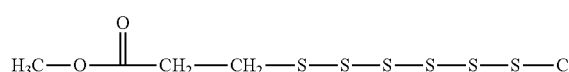
CAS: 862010-13-7

A number of proposed solutions have been devised for reducing rolling resistance. In DE 2 255 577 A and DE 4 435 311 A, EP-A 0 0670 347, and U.S. Pat. No. 4,709,065 polysulfidic silanes are described as reinforcing additives for silica-containing rubber vulcanizates. The property profile of the resultant rubber vulcanizates is not yet ideal. In particular, the abrasion values are disadvantageously high. High abrasion values can have a very disadvantageous effect on the lifetime of the products.

In the processing of rubbers it is advantageous for the rubber mixture initially prepared with the additives to have low viscosity (Mooney viscosity ML 1+4/100° C.), and thus to have good processability. Other additional substances have been proposed for improving the processability of silica-containing rubber mixtures, examples being fatty acid esters, fatty acid salts, and mineral oils. The additional substances mentioned have the disadvantage of that, although they increase flowability, they greatly reduce moduli at relatively high elongation (e.g. from 100% to 300%) or the hardness of the vulcanizates, thus impairing the reinforcing effect of the filler. Inadequate hardness or stiffness of the vulcanizate leads to unsatisfactory running performance of the tire, particularly around curves. The hardness of the vulcanizate can be increased by increasing the proportion of reinforcing filler, or by reducing the proportion of plasticizer oil, but each of these two measures has the disadvantage of causing higher mixture viscosity during processing.

EP 0 489 313 describes additives comprising glycol functions and having good mechanical properties and improved hysteresis performance. When comparison is made with bis[3-(triethoxysilyl)propyl] tetrasulfide, however, according to DE-OS (German Published Specification) 2 255 577, the examples reveal no improvement in rolling resistance (tan δ at 60° C.).

Arisawa et al. In Tetrahedron Letters, 2005, volume 46, edn, 28, pp. 4797-4800 describe the production of a polysulfide mixture based on the formula (I) via rhodium-catalyzed sulfur exchange.

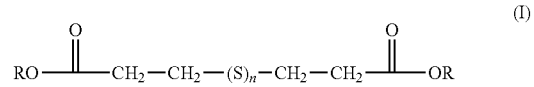

The polysulfide mixture disclosed comprises polysulfides of the formulae (II), (III), (IV), (V), and (VI):

CAS: 20707-94-2

CAS: 862010-12-6

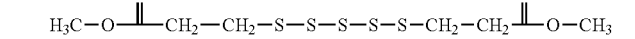

The polysulfide mixture disclosed by Arisawa et al. comprises about

| in mol % | in % by weight | |
|---|---|---|
| 49% | 44% | of compound (II) |
| 26% | 26% | of compound (III) |
| 14% | 16% | of compound (IV) |
| 7% | 9% | of compound (V) |
| 4% | 5% | of compound (VI). |

No practical use of the polysulfide mixture disclosed is described.

The high proportion of compound (II) also inhibits use in rubber mixtures. This has relatively low molecular weight (238.3), relatively taw flashpoint (150° C.), and a strong unpleasant odor. It moreover comprises only sulfur atoms bonded to at least one carbon atom, and comprises no sulfur atoms bonded only to sulfur atoms, the latter being more easily available for reactions and being termed hereinafter active sulfur atoms. The mixture disclosed by Arisawa et al. therefore comprises on average less than three sulfur atoms per molecule, and therefore comprises on average less than one active central sulfur atom per molecule.

The application EP 11164319, hitherto unpublished, describes the use of a polysulfide of the formula (IV) where R=methyl in silica-containing rubber mixtures. Repetition of the experiment disclosed revealed that EP 11164319 used, as polysulfide, a mixture which comprised 65% of the compound (IV) and 35% of the compounds (II), (III), (V), and (VI), in particular 31% of the compounds (III) and (V). The use of this polysulfide mixture achieved an improvement in Mooney viscosity and hardness, but at the cost of markedly increased rolling resistance and abrasion, and the polysulfide is therefore not ideal for the use in tires.

If is an object of the present invention to eliminate the disadvantages described of the prior art, and to find novel improved polysulfides mixtures and processes for production thereof, and thus to provide novel rubber mixtures which still have good flowability and which can be converted into vulcanizates which have significantly improved rolling resistance in conjunction with high hardness and low abrasion.

On the basis of the finding that when compounds of the formula (IV) are heated above 45° C. they readily disproportionate to give compounds having a larger and smaller number of sulfur atoms, a process has now been developed which provides polysulfide mixtures of the invention which, by virtue of a narrow distribution of the length of the sulfur chains in the mixture, are surprisingly capable of achieving the object of the invention.

In the process of the invention for the production of polysulfide mixtures, contact is effected between alkyl 3-mercaptopropionates (VII), production of which is described in a wide variety of references, and $S_2Cl_2$,

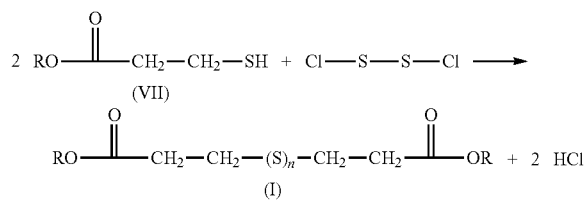

where each of the two moieties R is identical or different, preferably identical, and is methyl, ethyl, n-propyl, 2-propyl, n-butyl, isobutyl, tert-butyl, or $C_5$-alkyl, $C_6$-alkyl, $C_7$-alkyl, or $C_8$-alkyl, preferably methyl, ethyl, n-propyl, n-butyl, or isooctyl, particularly preferably methyl, and n is a number from 2 to 6.

In principle it is also possible to use various alkyl mercaptopropionates (VII), thus producing polysulfide mixtures which comprise asymmetric polysulfides, i.e. polysulfides which bear two different substituents R. For the purposes of the present invention, mixtures of this type are to be considered as equivalent to the mixtures of polysulfides having identical substituents R. The preferred embodiment of the present invention involves a polysulfide mixture of symmetrical polysulfides, i.e. involves polysulfides which bear two identical substituents, in particular mixtures in which R is identical in all of the polysulfides.

The contact between the materials typically takes place in an inert medium, and this means a medium which, under the reaction conditions, undergoes reaction with the reactants to an extent of at most 10%, preferably at most 5%, particularly preferably at most 1%, and very particularly preferably 0%. A suitable medium is preferably any of the following that are liquid under reaction conditions: aliphatic cyclic and/or acyclic hydrocarbons, aromatic hydrocarbons, aliphatic and/or aromatic halohydrocarbons, ethers, and esters, and mixtures thereof. Particularly preferred media are toluene and cyclohexane, it is preferable to use anhydrous media.

In one preferred embodiment, the materials are brought into contact in a mixture of polysulfides of the formula (I), in particular of the polysulfide mixtures of the invention described above, and it is thus possible to omit the removal of the inert medium.

it is preferable to use, as initial charge, a mixture of alkyl 3 mercaptopropionates (VII) and of inert medium, and then to meter $S_2Cl_2$ into the reaction mixture, with cooling of same. However, it is also possible to introduce the materials simultaneously into the inert medium. The process can be conducted either in batchwide mode, in continuous mode, in semicontinuous mode, or in cascade mode.

The contact between materials typically takes place at temperatures of from 0° C. to 60° C., preferably from 10° C. to 45° C., particularly preferably from 15° C. to 35° C. If temperatures are too low, $S_2Cl_2$ is not necessarily immediately consumed in the reaction, and this can lead to potential risks and to byproducts resulting from build-up of a relatively high concentration of $S_2Cl_2$ in the reaction mixture. Excessively high temperatures should likewise be avoided for reasons of occupational safety and of product quality.

It is preferable to carry out the reaction under inert gas. It is preferable to use noble gases or nitrogen for this purpose.

It is preferable that all or some of the resultant HCl gas is removed from the mixture before the end of the reaction, in particular via passage of inert gas through the reaction mixture and/or via application of vacuum, i.e. of a pressure of less than 1013 mbar.

If a polysulfide mixture of the invention is used as inert medium, removal of the inert medium is omitted. In other cases, i.e. when an inert medium other than a polysulfide mixture of the invention is used, the removal of said inert medium takes place at a temperature no higher than 45° C., preferably no higher than 40° C., particularly preferably no higher than 35° C., and very particularly preferably no higher than 30° C., and is preferably carried out at reduced pressure, i.e. less than 1013 mbar.

In one preferred embodiment, therefore, both the contact between alkyl 3-mercaptopropionates (VII) and $S_2Cl_2$ and the removal of an inert medium, insofar as this is not a polysulfide mixture of the invention, are effected in the temperature range from 10° C. to 45° C., particularly from 15° C. to 35° C., very particularly from 20° C. to 30° C.

The present invention provides not only the process for the production of polysulfide mixtures of the invention but also the resultant polysulfide mixtures of the formula (I), where the two moieties R are identical or different, preferably identical, and are methyl, ethyl, n-propyl, 2-propyl, n-butyl, isobutyl, tert-butyl, or $C_5$-alkyl, $C_6$-alkyl, $C_7$-alkyl, or C8-alkyl preferably methyl, ethyl, n-propyl, n-butyl, or isooctyl, particularly preferably methyl, and n is a number from 2 to 6.

The polysulfide mixtures of the invention comprise at least 80%, preferably at least 85%, particularly preferably at least 90%, and very particularly preferably from 95 to 99%, of one or more polysulfide compounds of the formula (I) where n=4, based on the total quantity of polysulfide compounds of the formula (I). For the purposes of the present application, the quantitative data relating to the compounds of the formula (I) are area percentage data from the type of HPLC measurement described near the end of example 3, using refractive index (RI) defector.

The polysulfide mixture of the invention usually comprises less than 10%, preferably less than 6%, particularly preferably less than 4%, and very particularly preferably less than 2%, of polysulfide compounds of the formula (I) where n=3, based on the total quantity of polysulfide compounds of the formula (I).

The polysulfide mixture of the invention usually comprises less than 10%, preferably less than 6%, particularly preferably less than 4%, and very particularly preferably less than 3%, of polysulfide compounds of the formula (I) where n=5, based on the total quantity of polysulfide compounds of the formula (I).

The polysulfide mixture of the invention usually comprises less than 10%, preferably less than 5%, particularly preferably less than 2%, and very particularly preferably less than 1%, of polysulfide compounds of the formula (I) where n=2, based on the total quantity of polysulfide compounds of the formula (I).

The polysulfide mixture of the invention usually comprises less than 3%, preferably less than 2%, and very particularly preferably no more than 1%, of polysulfide compounds of the formula (I) where n=6, based on the total quantity of polysulfide compounds of the formula (I).

The polysulfide mixture of the invention also comprises, alongside one or more compounds of the formula (I) where n=4, one or more of the compounds of the formula (I) where n=2, 3, 5, or 6. The total proportion of the compounds of the formula (I) where n=2, 3, 5, and 6 is usually no more than 20%, preferably no more than 15%, particularly preferably no more than 10%, and very particularly preferably from 1 to 5%, based on the total quantity of polysulfide compounds of the formula (I), in the corresponding mixture.

In one preferred embodiment, the polysulfide mixture of the invention comprises less than 10%, particularly less than 3%, very particularly less than 1%, and most preferably less than 0.2%, of byproducts or admixtures, i.e. compounds which do not correspond to the formula (I).

The polysulfide mixture of the invention typically comprises less than 2%, preferably less than 1%, particularly preferably lass than 0.3%, very particularly preferably less than 0.1%, and most preferably 0%, of elemental sulfur as admixture.

The flashpoint of a polysulfide mixture of the invention is usually above 180° C., preferably above 200° C.

The sulfur content of the polysulfide mixture of the invention is usually, from elemental analysis, from 35 to 50%, preferably from 40 to 45%.

The typical total chlorine content of a polysulfide mixture of the invention is <1000 ppm, preferably <100 ppm, particularly preferably <10 ppm.

The number of sulfur atoms in the polysulfide mixture of the invention is usually on average, per molecule of the formula (I), from 3.5 to 4.5, preferably from 3.7 to 4.3, particularly preferably from 3.8 to 4.2, very particularly preferably from 3.9 to 4.1. The number of active sulfur atoms in the polysulfide mixture of the invention is therefore typically on average, per molecule of the formula (I), from 1.5 to 2.5, preferably from 1.7 to 2.3, particularly preferably from 1.8 to 2.2, very particularly preferably from 1.9 to 2.1.

After production of the polysulfide mixtures of the formula (I) of the invention, they are preferably stored at temperatures of from 0 to 35° C., in particular from 0 to 20° C.

The polysulfide mixtures of the invention exhibit unexpected properties when used in rubber mixtures, in comparison with a reference mixture without the polysulfide mixture of the invention, there was an improvement in flowability and scorch time of the mixture, and in the hardness and the rolling resistance of the vulcanizate. This is all the more astounding because the mixture used in EP 11164319 comprising 65% of the compound (IV) and 31% of the compounds (III) and (V), i.e. comprising comparable content of active sulfur atoms, causes marked impairment of rolling resistance and abrasion in comparison with the reference mixture.

The invention therefore also provides rubber mixtures comprising respectively at least one rubber and one polysulfide mixture of the invention.

In particular, the invention provides rubber mixtures comprising respectively at least one rubber, one sulfur-containing alkoxysilane, one silica-based filler, and one polysulfide mixture of the invention.

The polysulfide mixtures of the invention can also to some extent or entirely be used after absorption on inert, organic, or inorganic carriers. Preferred carrier materials are silica, natural and synthetic silicates, aluminum oxide, and/or carbon blacks.

The total content of polysulfide mixture of the invention in the rubber mixtures in the invention is preferably from 0.1 to 15 phr, particularly from 0.3 to 7 phr, very particularly from 0.5 to 3 phr, and most preferably from 0.7 to 1.5 phr. The unit phr represents parts by weight based on 100 parts by weight of rubber used in the rubber mixture.

Natural rubber and/or synthetic rubbers can be used for the production of the rubber mixtures of the invention. Examples of preferred synthetic rubbers are:

BR polybutadiene
ABR butadiene/$C_1$-C4-alkyl acrylate copolymer
CR polychloroprene
IR polyisoprene
SBR styrene/butadiene copolymers with styrene contents of from 1 to 60%, preferably from 20 to 50% by weight
IIR isobutylene/isoprene copolymers
NBR butadiene/acrylonitrile copolymers with from 5 to 60% by weight, preferably from 10 to 50% by weight, acrylonitrile content
HNBR partially or fully hydrogenated NBR rubber
EPDM ethylene/propylene/diene copolymers
and mixtures of two or more of these rubbers.

It is preferable that the rubber mixtures of the invention comprise at least one SBR rubber and at least one BR rubber, particularly in an SBR:BR ratio by weight of from 60:40 to 90:10.

In one advantageous embodiment, the rubber mixtures of the invention moreover comprise at least one NR rubber. It is particularly preferable that they comprise at least one SBR rubber, at least one BR rubber, and at least one NR rubber, where the ratio by weight of SBR rubber to BR rubber to NR rubber is very particularly preferably from 60 to 85; from 10 to 35: from 5 to 20.

Examples of sulfur-containing alkoxysilanes suitable for the rubber mixtures of the invention are bis(triethoxysilylpropyl) tetrasulfane (e.g. Si 69 from Evonik) and bis(triethoxysilylpropyl) disulfane (e.g. Si 75 from Evonik), 3-(triethoxysilyl)-1-propanethiol, polyether-functionalized mercaptosilanes such as Si 363 from Evonik, and thioester-functionalized alkoxysilanes such as NXT or NXT Z from Momentive (previously GE). It is also possible to use mixtures of the sulfur-containing alkoxysilanes. Liquid sulfur-containing alkoxysilanes may be applied to a support in order to increase ease of metering and/or dispersibility (dry liquid). The active ingredient content is between 30 and 70 parts by weight, preferably 40 and 60 parts by weight, per 100 parts by weight of dry liquid.

The proportion of the sulfur-containing alkoxysilanes in the inventive rubber mixtures is preferably 2 to 20 phr, more preferably 3 to 11 phr and most preferably 5 to 8 phr, calculated in each case as 100% active ingredient. It is preferable that the quantity of sulfur-containing alkoxysilane is greater than or equal to the quantity of the polysulfide mixture of the formula (I) of the invention. The ratio by weight of sulfur-containing alkoxysilane to the polysulfide mixture of the formula (I) of the invention is particularly preferably from 1.5:1 to 20:1, very particularly preferably from 3:1 to 15:, and most preferably from 5:1 to 10:1.

The rubber mixture preferred in the invention moreover comprises one or more silica-based fillers. Substances preferably used here are the following:

- silica, in particular precipitated silica or fumed silica, produced for example via precipitation of solutions of silicates or flame hydrolysis of silicon halides with specific surface areas of from 5 to 1000 m$^2$/g, preferably from 20 to 400 m$^2$/g (BET surface area) and with primary particle sizes of from 10 to 400 nm. The silicas can optionally also take the form of mixed oxides with other metal oxides such as oxides of Al, of Mg, of Ca, of Ba, of Zn, of Zr, or of Ti.
- synthetic silicates such as aluminum silicate, alkaline earth metal silicates such as magnesium silicate or calcium silicate, with BET surface areas of from 20 to 400 m$^2$/g and primary particle size of from 10 to 400 nm,
- natural silicates such as kaolin and other naturally occurring silicas,
- glass fibers including those in the form of mats and strands,
- glass microspheres.

It is of course possible to use additional fillers. Carbon blacks produced by the lamp-black, furnace-black, or gas-black process are particularly suitable for this purpose where the BET surface areas of these are from 20 to 200 m$^2$/g, examples being SAF, ISAF, IISAF, HAF, FEF, and GPF carbon blacks.

The total content of fillers is preferably from 10 to 200 phr, particularly preferably from 50 to 160 phr, and very particularly preferably from 60 to 120 phr.

A particularly preferred embodiment is provided by the combination of silica, carbon black, and polysulfide mixture of the invention. The ratio of silica to carbon black here can vary within any desired limits, but for the application in tires preference is given to a silica:carbon black ratio by weight of from 20:1 to 1.5:1.

In one preferred embodiment, the rubber mixtures of the invention also comprise one or more crosslinking agents. Sulfur-based or peroxidic crosslinking agents are particularly suitable for this purpose, and particular preference is given here to sulfur-based crosslinking agents.

Peroxidic crosslinking agents preferably used are bis(2,4-dichlorobenzyl) peroxide, dibenzoyl peroxide, bis(4-chlorobenzoyl) peroxide, 1,1-bis(tert-butylperoxy)-3,3,5-trimethylcyclohexane, tert-butyl perbenzoate, 2,2-bis(tert-butylperoxy)butanes 4,4-di-tert-butylperoxynonyl valerate, dicumyl peroxide, 2,5-dimethyl-2,5-di(tert-butylperoxy) hexane, tert-butyl cumyl peroxide, 1,3-bis(tert-butylperoxyisopropyl)benzene, di-tert-butyl peroxide, and 2,5-dimethyl-2,5-di(tert-butylperoxy)-3-hexyne.

Other additions that can also be used with advantage, alongside these peroxidic crosslinking agents, are those that can increase crosslinking yield: examples of compounds suitable for this purpose are triallyl isocyanurate, triallyl cyanurate, trimethylolpropane tri(meth)acrylate, triallyl trimellitate, ethylene glycol di(meth)acrylate, butanediol di(meth)acrylate, trimethylolpropane tri(meth)acrylate, zinc diacrylate, zinc dimethacrylate, 1,2-polybutadiene, and N,N'-m-phenylenedimaleimide.

Sulfur can be used as crosslinking agent in elemental soluble or insoluble form, or in the form of sulfur donors. Examples of sulfur donors that can be used are dimorpholyl disulfide (DTDM), 2-morpholinodithiobenzothiazole (MBSS), caprolactam disulfide, dipentamethylenethiuram tetrasulfide (DPTT), and tetramethylthiuram disulfide (TMTD).

The crosslinking of the rubber mixtures of the invention can in principle be achieved with sulfur or sulfur donors alone, or in conjunction with vulcanization accelerators, examples of compounds suitable for these being dithiocarbamates, thiurams, thiazoles, sulfenamides, xanthogenates, bi- or polycyclic amines, guanidine derivatives, dithiophosphates, caprolactams, and thiourea derivatives. Other compounds suitable are moreover zinc diamine diisocyanate, hexamethylenetetramine, 1,3-bis(citraconimidomethyl)benzene, and also cyclic disulfanes. It is preferable that the rubber mixtures of the invention comprise sulfur-based crosslinking agents and vulcanization accelerators.

Crosslinking agents particularly preferably used are sulfur, magnesium oxide, and/or zinc oxide; the known vulcanization accelerators such as mercaptobenzothiazoles, thiazolsulfenamides, thiurams, thiocarbamates, guanidines, xanthogenates, and thiophosphates are added to these.

Preferred quantities used of the crosslinking agents and vulcanization accelerators are from 0.1 to 10 phr, particularly from 0.1 to 5 phr.

The rubber mixtures of the invention can comprise other rubber auxiliaries, such as reaction accelerators, aging inhibitors, heat stabilizers, light stabilizers, antioxidants, and in particular antiozonants, flame retardants, processing aids, impact-resistance improvers, plasticizers, tackifiers, blowing agents, dyes, pigments, waxes, extenders, organic acids, retarders, metal oxides, and activators, in particular triethanolamine, polyethylene glycol, hexanetriol, and anti-reversion agents.

The quantities used of these rubber auxiliaries are conventional, depending inter alia on the intended purpose of the vulcanizates. Conventional quantities are from 0.1 to 30 phr.

Preferred aging inhibitors used are alkylated phenols, styrenated phenol, sterically hindered phenols such as 2,6-di-tert-butylphenol, 2,6-di-tert-butyl-p-cresol (BHT), 2,6-di-tert-butyl-4-ethylphenol, sterically hindered phenols containing ester groups, sterically hindered phenols containing thioether, 2,2'-methylenebis-(4-methyl-6-tert-butylphenol) (BPH), and also sterically hindered thiobisphenols.

If discoloration of the rubber is not important, it is also possible to use aminic aging inhibitors, e.g. mixtures of diaryl-p-phenylenediamines (DTPD), octylated diphenylamine (ODPA), phenyl-α-naphthylamine (PAN), phenyl-β-naphthylamine (PBN), preferably those based on phenylenediamine, e.g. N-isopropyl-N'-phenyl-p-phenylanediamine, N-1,3-dimethylbutyl-N'-phenyl-p-phenylenediamine (6PPD), N-1,4-dimethylpentyl-N'-phenyl-p-phenylenediamine (7PPD), N,N'-bis(1,4-dimethylpentyl)-p-phenylenediamine (77PD).

Other aging inhibitors are phosphites such as tris(nonylphenyl) phosphite, polymerized 2,2,4-trimethyl-1,2-dihydroquinoline (TMQ), 2-mercaptobenzimidazole (MBI), methyl-2-mercaptobenzimidazole (MMBI), zinc methylmercaptobenzimidazole (ZMMBI), these mostly being used in combination with above phenolic aging inhibitors. TMQ, MBI, and MMBI are mainly used for NBRs, where these are vulcanized peroxidically.

Ozone resistance can be improved via antioxidants such as N-1,3-dimethylbutyl-N'-phenyl-p-phenylenediamine (6PPD), N-1,4-dimethylpentyl-N'-phenyl-p-phenylenediamine (7PPD), N,N'-bis(1,4-dimethylpentyl)-p-phenylenediamine (77PD), enol ethers, or cyclic acetals.

Processing aids are intended to act between the rubber particles, and to counteract frictional forces during mixing, plastification, and deformation. Processing auxiliaries which may be present in the rubber mixtures of the invention comprise all the lubricants conventionally used for the processing of plastics, for example hydrocarbons such as oils, paraffins and PE waxes, fatty alcohols having from 6 to 20 carbon atoms, ketones, carboxylic acids such as fatty acids and montan acids, oxidized PE wax, metal salts of carboxylic acids, carboxamides, and carboxylic esters, for example with the alcohols ethanol, fatty alcohols, glycerol, ethanediol, pentaerythritol, and long-chain carboxylic acids as acid component.

The rubber mixture composition of the invention can also comprise flame retardants in order to reduce flammability, and to reduce smoke generation during combustion. Examples of compounds used for this purpose are antimony trioxide, phosphoric esters, chloroparaffin, aluminum hydroxide, boron compounds, zinc compounds, molybdenum trioxide, ferrocene, calcium carbonate, and magnesium carbonate.

It is also possible to add other plastics to the rubber vulcanizate prior to crosslinking, these acting by way of example, as polymeric processing aids or as impact modifiers. These plastics are preferably selected from the group consisting of homo- and copolymers based on ethylene, propylene, butadiene, styrene, vinyl acetate, vinyl chloride, glycidyl acrylate, glycidyl methacrylate, or on acrylates or methacrylates having alcohol components of branched or unbranched $C_1$ to $C_{10}$ alcohols, particular preference being given to polyacrylates having identical or different alcohol moieties from the group of the $C_4$ to $C_8$ alcohols, in particular of butanel, hexanol, octanol and 2-ethylhexanol, and to polymethyl methacrylate, methyl methacrylate-butyl acrylate copolymers, methyl methacrylate-butyl methacrylate copolymers, ethylene-vinyl acetate copolymers, chlorinated polyethylene, ethylene-propylene copolymers, and ethylene-propylene-diene copolymers.

In one preferred embodiment, the rubber mixture of the invention comprises from 0.1 to 15 phr of the anti-reversion agent 1,6-bis(N,N-dibenzylthiocarbamoyldithio)hexane (CAS No.; 151900-44-6), permitting a further reduction in rolling resistance.

A preferred feature of the rubber mixtures of the Invention is that the loss factor tan δ at 60° C. of a vulcanizate produced therefrom under 170° C./t95 heating conditions is <0.12, while its Shore A hardness at 23° C. is >68. In combination therewith, the inventive rubber mixtures can also achieve a vulcanization time of less than 2000 seconds, and particularly preferably a scorch time of from 500 to 1000 seconds.

The present invention further provides a process for the production of rubber mixtures via mixing of at least one rubber with a polysulfide mixture of the invention. It is moreover preferable to admix at least one silica-based filler, and at least one sulfur-containing alkoxysilane. It is preferable here to use from 10 to 150 phr of filler, particularly from 30 to 120 phr, and very particularly from 50 to 100 phr, from 0.1 to 15 phr of polysulfide mixture of the invention, particularly from 0.3 to 7 phr, very particularly from 0.5 to 3 phr, and most preferably from 0.7 to 1.5 phr, and from 2 to 20 phr of the sulfur-containing alkoxysilane, particularly from 3 to 11 phr, and very particularly from 5 to 8 phr. In the mixing process it is moreover possible to add the above-mentioned additional fillers, crosslinking agents, vulcanization accelerators, and rubber auxiliaries, preferably in the quantities stated above.

In the multistage mixing process, the addition of the polysulfide mixture of the invention preferably takes place in the first part of the mixing process, the addition of one or more crosslinking agents, in particular sulfur, and optionally vulcanization accelerators, taking place in a subsequent mixing stage. The temperature of the rubber composition here is preferably from 100 to 20° C., particularly preferably from 120° C. to 170° C. The shear rates for the mixture during mixing are from 1 to 1000 $sec^{-1}$, preferably from 1 to 100 sec−1. In one preferred embodiment, the rubber mixture is cooled after the first mixing stage, and the crosslinking agent and optionally crosslinking accelerator, and/or additions used to increase crosslinking yield are added in a subsequent mixing stage at <140° C., preferably <100° C. It is equally possible to add the polysulfide mixture of the invention in a subsequent mixing stage and at relatively low temperatures, for example from 40 to 100° C., for example together with sulfur and crosslinking accelerator.

Conventional mixing assemblies, such as rolls, internal mixers, and mixing extruders, can be used to blend the rubber with the filler and with the polysulfide mixture of the invention.

The optional addition of 1,6-bis(N,N-dibenzylthiocarbamoyldithio)hexane preferably takes place in the first stage of the multistage mixing process.

The present invention further provides a process for the vulcanization of the rubber mixtures of the invention which is preferably carried out with temperatures of the composition of from 100 to 200° C., particularly from 130 to 180° C. In one preferred embodiment, the vulcanization takes place at a pressure of from 10 to 200 bar.

The present invention also comprises rubber vulcanizates obtainable via vulcanization of the rubber mixtures of the invention. The present invention further comprises rubber products comprising said vulcanizates. In particular tires, since corresponding tires have the advantage of high hardness coupled with good rolling resistance.

When vehicles, in particular motor vehicles, are equipped with tires which comprise the vulcanizates of the invention, this leads to lower energy consumption during the operation of these vehicles, thus permitting lower fuel consumption in the case of motor vehicles with internal combustion engines and greater range in the case of vehicles with electric drive, and less effort and/or higher velocity in the case of vehicles driven by muscle power. The present invention therefore also comprises vehicles comprising rubber products which include the vulcanizates of the invention.

The rubber vulcanizates of the invention are suitable for the production of moldings with improved properties, e.g. for the production of cable sheathing, of fuses, of drive belts, of conveyor belts, of roll coverings, of tires, of shoe soles, of sealing rings, and of damping elements.

The rubber vulcanizate of the invention can moreover be used for the production of foams. For this, chemical or physical blowing agents are added thereto. Any of the substances known for this purpose can be used as chemical blowing agents, for example azodicarbonamide, p toluenesulfonyl hydrazide, 4,4'-oxybis(benzenesulfohydrazide), p-toluenesulfonyl semicarbazide, 5-phenyltetrazole, N,N'-dinitrosopentamethylenetetramine, zinc carbonate, or sodium hydrogencarbonate, and mixtures comprising these substances. Examples of suitable physical blowing agents are carbon dioxide and halogenated hydrocarbons.

The present invention further provides the use of the polysulfide mixture of the invention for the production of rubber mixtures, and of vulcanizates thereof, and in particular for the production of rubber mixtures comprising at least respectively one rubber, one sulfur-containing alkoxysilane, and one silica-based filler.

The present invention further provides the use of the polysulfide mixture of the invention for the production of additive compositions for rubbers.

Surprisingly, it has been found that additive compositions for rubbers comprising at least one sulfur-containing alkoxysilane, in particular bis(triethoxysilylpropyl) tetrasulfane, bis(triethoxysilylpropyl) disulfane, 3-(triethoxysilyl)-1-propanethiol, polyether-functionalized mercaptosilane, or thioester-functionalized alkoxysilane, and the polysulfide mixture of the invention have sufficient compatibility of the components, despite the reactive groups, thus permitting homogeneous incorporation into rubber mixtures and precise metering in the desired ratio. The present invention therefore also comprises additive compositions of this type for rubbers, and also the use of the polysulfide mixtures of the invention for the production of additive compositions of this type. The ratio by weight of alkoxysilane, in particular of bis(triethoxysilylpropyl) tetrasulfane and/or of bis(triethoxysilylpropyl) disulfane, to the polysulfide mixtures of the invention in these additive compositions is preferably from 1.5:1 to 20:1, particularly preferably from 3:1 to 15:1, and very particularly preferably from 5:1 to 10:1.

The present invention moreover comprises a process for the production of additive compositions for rubbers, characterized in that sulfur-containing alkoxysilanes are mixed with the polysulfide mixtures of the invention.

The present invention further comprises a process for reducing the rolling resistance of tires, where a polysulfide mixture of the invention is mixed with a non-crosslinked or partially crosslinked rubber mixture serving as starting material for at least parts of the tire, and the mixture is then vulcanized.

Determination of the Properties of Rubber Mixture and of Vulcanizates:

Measurement of Mooney Viscosity:

The viscosity can be determined directly from the force with which the rubbers (and rubber mixtures) resist processing thereof. In the Mooney shearing disk viscometer, a fluted disk is enclosed, above and below, by test substance and is rotated at about two revolutions per minute in a beatable chamber. The force required here is measured in the form of torque, and corresponds to the respective viscosity. The sample is generally preheated for one minute to 100° C.; the measurement takes a further 4 minutes, the temperature being kept constant here. The viscosity is stated together with the respective test conditions, an example being ML (1+4) 100° C. (Mooney viscosity, large rotor, preheat time and test time in minutes, test temperature).

Scorch Performance (Scorch Time t5):

The same test can moreover be used as described above to measure the scorch performance of a mixture. The selected temperature was 130° C. The rotor runs until, after the torque value has passed through a minimum, it has increased to 5 Mooney units above the minimum value (t5). The greater the value (unit being seconds), the slower the scorch. A scorch time that is advantageous for practical purposes is mostly more than 300 seconds, and when minimization of processing risk and the cost of time are taken into account this should be less than 1000 seconds.

170° C./t95 Full Vulcanization Time From Rheometer (Vulcameter):

The MDR (moving die rheometer) vulcanization profile and analytical data associated therewith are measured in a MDR 2000 Monsanto rheometer in accordance with ASTM D5289-95. The full vulcanization time determined is the time at which 95% of the rubber has been crosslinked. The selected temperature was 170° C.

Hardness Determination:

The hardness of the rubber mixture of the invention was determined by producing milled sheets of thickness 6 mm from the rubber mixture in accordance with formulations of table 1. Test samples of diameter 35 mm were out from the milled sheets, and the Shore A hardness of these was determined by using a digital Shore hardness tester (Zwick GmbH & Co. KG, Ulm). The hardness of a rubber vulcanizate provides a first indication of its stiffness.

Tensile Test:

The tensile test serves directly to determine the loading limits of an elastomer, and is carried out in accordance with DIN 53504. The increase in length at break is divided by the initial length to give elongation at break. The force required for particular stages of elongation, mostly 50, 100, 200, and 300%, is also determined, and expressed as modulus (tensile strength at the stated elongation of 300%, or 300 modulus).

Dyn. Damping:

Dynamic test methods are used to characterize the deformation behavior of elastomers under periodically changing loads. An externally applied stress changes the conformation of the polymer chain. The loss factor tan δ is determined indirectly here by way of the ratio of loss modulus G" to storage modulus G'. The loss factor tan δ at 60° C. is associated with rolling resistance and should be as low as possible.

Abrasion:

Abrasion gives an indication of wear, and thus of product lifetime. Abrasion was determined in accordance with DIN 53516. A low value is desirable for economic and environmental reasons.

EXAMPLE 1

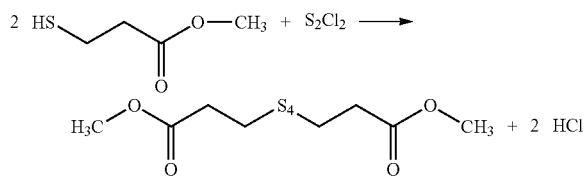

Apparatus: 500 ml four-necked flask with thermometer, dropping funnel with pressure equalizer, reflux condenser with gas outlet attachment (bubble counter), and hose, stirrer, gas inlet tube Initial charge: 92 g (0.75 mol) of methyl 3-mercaptopropionate (Acros, ≥98%)

250 ml of cyclohexane (p.A., Merck dried over molecular sieve)

Feed: 51.2 g (0.375 mol) of disulfur dichloride (≥99%, from Merck)

Dry cyclohexane and methyl 3-mercaptopropionate were used as initial charge in the nitrogen-purged apparatus. Once the methyl 3-mercaptopropionate had dissolved completely, the disulfur dichloride was added dropwise within about 1 h at a temperature of from 5-10° C. while nitrogen was passed through the system. Adjustment of metering rate was such that a temperature of 10° C. was not exceeded. Once the reaction had ended, stirring of the mixture was continued overnight at room temperature while nitrogen was passed through the system. The reaction solution was then concentrated at 50° C. on a rotary evaporator, and drying was continued at 60° C. in a vacuum drying oven to constant weight.

Yield: 108.4 g (95.6%) of a polysulfide mixture of the idealized formula

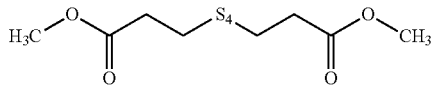

Elemental Analysis:
C:31.9% H:5.3% O:21.7% S: 42.0%

The product was analyzed by RP-HPLC and time-of-flight mass spectrometry (TOF MS).

The percentage data for the compounds of the formula (I) are derived from the HPLC area percentages, using RI detector.

<1% of compound (II), 16% of compound (III), 65% of compound (IV), 15% of compound (V), 4% of compound (VI)

EXAMPLE 2

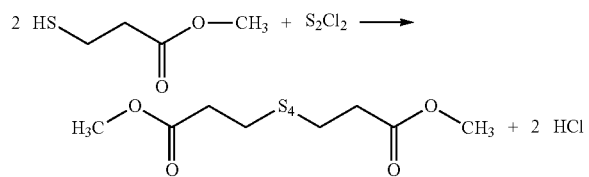

Apparatus: 500 ml four-necked flask with thermometer, dropping funnel with pressure equalizer, reflux condenser with gas outlet attachment (bubble counter), and hose, stirrer, gas inlet tube Initial charge: 92 g (0.75 mol) of methyl 3-mercaptopropionate (Acros, ≥98%)
250 ml of cyclohexane (p.A., Merck dried over molecular sieve)
Feed: 51.2 g (0.375 mol) of disulfur dichloride (≥99%, from Merck)

Dry cyclohexane and methyl 3-mercaptopropionate were used as initial charge in the nitrogen-purged apparatus. Once the methyl 3-mercaptopropionate had dissolved completely, the disulfur dichloride was added dropwise within about 30 min at a temperature of from 20-25° C. while nitrogen was passed through the system. Adjustment of metering rate was such that a temperature of 25° C. was not exceeded. Once the reaction had ended, stirring of the mixture continued overnight at room temperature while nitrogen was passed through the system. The reaction solution was then concentrated at 30° C. on a rotary evaporator.

Yield: 115 g (101.4%) of a polysulfide mixture of the idealized formula

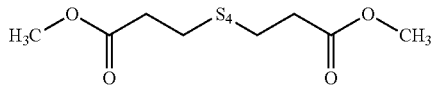

The quantities used of the starting materials are based on the minimum content guaranteed by the manufacturer, e.g. ≥98%. Because actual purities of the starting materials were higher, and because of inaccuracies due to rounding, the calculated yield was slightly above 100%.

Elemental analysis:
C:31.9% H:4.5% O:21.7% S:42.1% Cl:<10 ppm

The product was analyzed by RP-HPLC and time-of-flight mass spectrometry (TOF MS).

The percentage data for the compounds of the formula (I) are derived from the HPLC area percentages, using RI detector.

<1% of compound (II), 1% of compound (III), 96% of compound (IV), 2% of compound (V), <1 % of compound (VI)

EXAMPLE 3

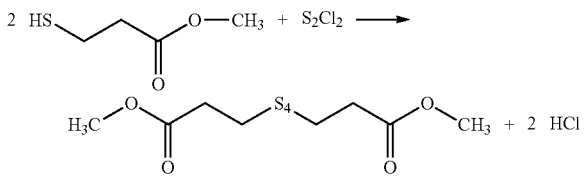

Apparatus: 500 ml four-necked flask with thermometer, dropping funnel with pressure equalizer, reflux condenser with gas outlet attachment (bubble counter), and hose, stirrer, gas inlet tube Initial charge; 92 g (0.75 mol) of methyl 3-mercaptopropionate (Acros, ≥98%)
200 g of polysulfide mixture produced by analogy with Example 2
Feed: 51.2 g (0.375 mol) of disulfur dichloride (≥99%, from Merck)

The polysulfide mixture (produced by analogy with Example 2) and methyl 3-mercaptopropionate were used as initial charge in the nitrogen-purged apparatus. Once the methyl 3-mercaptopropionate had dissolved completely, the disulfur dichloride was added dropwise within about 30 min at a temperature of from 20-25° C. while nitrogen was passed through the system. Adjustment of metering rate was such that a temperature of 25° C. was not exceeded. Once the reaction had ended, stirring of the mixture was continued overnight at room temperature while nitrogen was passed through the system. Treatment of the reaction solution then continued on a rotary evaporator at about 30° C. for 2 h.

Yield: 200 g+115 g (101.4%) of a polysulfide mixture of the idealized formula

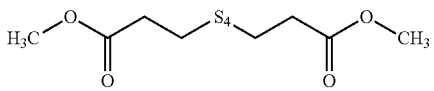

Elemental analysis:
C:32.0% H:4.8% O:21.8% S:41.9% Cl:<10 ppm

The product was analyzed by RP-HPLC. The percentage data for the compounds of the formula (I) are derived from the HPLC area percentages, using RI detector.

<1% of compound (II), 1% of compound (III), 96% of compound (IV), 2% of compound (V), <1% of compound (VI)

HPLC system with vacuum degasser, pump, column oven, injection system, and RI detector.

Column type: Eclipse XDB-C8, 5 μm
Column length: 150 mm
Internal column diameter: 4.6 mm
Mobile phase: 33% of water, 67% of methanol
Column temperature: 35° C.
Flow rate: 0.8 ml/min
Elution time: 30 min
Injection volume: 2 μl
RI detector: Agilent 1100 series G1362A 10 ml of tetrahydrofuran were used as initial charge in a 25 ml beaded-rim bottle, and about 300 μl of the sample were added, the mixture was homogenized, and chromatography of the solution then followed directly. Evaluation gives the area percentages.

Production of Rubber Mixtures and of Rubber Vulcanizates

The rubber formulations listed in table 1 were respectively mixed in accordance with multistage processes described below.

1st mixing stage:
BUNA® CB 24 and BUNA® VSL 5025-2 were used as initial charge in an internal mixer and mixed for about 30 seconds
addition of two thirds of VULKASIL® S, two thirds of SI® 69, and two thirds of the total quantity of polysulfide mixture of the invention, and mixing for about 60 seconds
addition of one third of VULKASIL® S, one third of SI® 69, and one third of the total quantity of polysulfide mixture of the invention, and TUDALEN 1849-1, and mixing for about 60 seconds
addition of CORAX® N 339, EDENOR® C 18 98-100, VULKANOX® 4020/LG, VULKANOX® HS/LG, ROTSIEGEL ZINC WHITE, and also ANTILUX® 654, and mixing for about 60 seconds. The mixing temperature was 150° C.

2nd mixing stage:
After conclusion of the first mixing stage, the mixture was passed to a downstream roll mill, shaped to give a sheet, and stored for 24 hours at room temperature. The processing temperatures here were below 60° C.

3rd mixing stage:
The third mixing stage involved further mastication at 150° C. in a kneader.

4th mixing stage:
Addition of the additional substances CHANCEL 90/95 GROUND SULFUR, VULKACIT® CZ/C, VULKACIT® D/C on a roll at temperatures below 80° C.

The rubber mixtures were then fully vulcanized at 170° C. Table 2 gives the properties of the rubber preparations produced and of vulcanizates of these.

TABLE 1

| Rubber formulation | | | | |
|---|---|---|---|---|
| | Reference | Rubber formulation 1 | Rubber formulation 2 | Rubber formulation 3 |
| BUNA CB 24 | 30 | 30 | 30 | 30 |
| BUNA VSL 5025-5 | 96 | 96 | 96 | 96 |
| CORAX N 339 | 6.4 | 6.4 | 6.4 | 6.4 |
| VULKASIL S | 80 | 80 | 80 | 80 |
| TUDALEN 1849-1 | 8 | 8 | 8 | 8 |
| EDENOR C 18 98-100 | 1 | 1 | 1 | 1 |
| VULKANOX 4020/LG | 1 | 1 | 1 | 1 |
| VULKANOX HS/LG | 1 | 1 | 1 | 1 |
| ROTSIEGEL ZINC WHITE | 2.5 | 2.5 | 2.5 | 2.5 |
| ANTILUX 654 | 1.5 | 1.5 | 1.5 | 1.5 |
| SI 69 | 6.4 | 6.4 | 6.4 | 6.4 |
| VULKACIT D/C | 2 | 2 | 2 | 2 |
| VULKACIT CZ/C | 1.5 | 1.5 | 1.5 | 1.5 |
| CHANCEL 90/95 GROUND SULFUR | 1.5 | 1.5 | 1.5 | 1.5 |
| Compound 1 | | 1 | | |
| Compound 2 | | | 1 | |
| Compound 3 | | | | 1 |

Quantitative Data in Phr (Parts by Weight Per 100 Parts of Rubber)

| Trade name | Description | Producer/Marketed by |
|---|---|---|
| BUNA CB 24 | BR | Lanxess Deutschland GmbH |
| BUNA VSL 5025-2 | SBR | Lanxess Deutschland GmbH |
| CORAX N 339 | Carbon black | Degussa-Evonik GmbH |
| VULKASIL S | Silica | Lanxess Deutschland GmbH |
| TUDALEN 1849-1 | Mineral oil | Hansen&Rosenthal KG |
| EDENOR C 18 98-100 | Stearic acid | Cognis Deutschland GmbH |
| VULKANOX 4020/LG | N-1,3-Dimethylbutyl-N-phenyl-p-phenylenediamine | Lanxess Deutschland GmbH |
| VULKANOX HS/LG | Polymerized 2,2,4-trimethyl-1,2-dihydroquinoline | Lanxess Deutschland GmbH |
| ROTSIEGEL ZINC WHITE | Zinc oxide | Grillo Zinkoxid GmbH |
| ANTILUX 654 | Light-stabilizer wax | RheinChemie Rheinau GmbH |
| SI 69 | Bis(triethoxysilylpropyl) tetrasulfide | Evonik Industries |
| VULKACIT D/C | 1,3-Diphenylguanidine | Lanxess Deutschland GmbH |
| VULKACIT CZ/C | N-Cyclohexyl-2-benzothiazolesulfenamide | Lanxess Deutschland GmbH |
| CHANCEL 90/95 GROUND SULFUR | Sulfur | Solvay Deutschland GmbH |

TABLE 2

| | | | | Rubber formulation | Rubber formulation |
| Parameter | Unit | DIN | Reference | 1 | 2 |
|---|---|---|---|---|---|
| Mooney viscosity (ML 1 + 4) | [MU] | 53523 | 95 | 82 | 87 |
| Mooney scorch for 130° C. (t5) | Sec | ASTM D5289-95 | 1253 | 1244 | 884 |
| Full vulcanization for 170° C./t95 | Sec | 53529 | 1417 | 1617 | 1648 |
| Shore A hardness at 23° C. | [Shore A] | 53505 | 66 | 72 | 69 |
| 300 modulus | MPa | 53504 | 15 | 17 | 14 |
| Elongation at break | % | 53504 | 349 | 346 | 350 |
| Tensile strength | MPa | 53504 | 19 | 20 | 17 |
| Abrasion | mm | 53516 | 74 | 95 | 73 |
| Rolling resistance (tan δ (60° C.)) | — | | 0.133 | 0.168 | 0.107 |

What is claimed is:

1. A polysulfide mixture comprising two or more compounds of the formula (I),

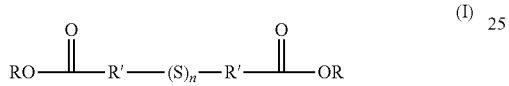

where
each R' is a $C_2$-alkylene;
each of the two moieties R is identical or different, and is methyl, ethyl, n-propyl, 2-propyl, n-butyl, isobutyl, tert-butyl, or $C_5$-$C_8$ alkyl; and
for at least one of the two or more compounds, n is 4, and for others of the two or more compounds, n is 2, 3, 5 or 6,
wherein:
the polysulfide mixture comprises a first proportion (x mol %) of the compounds of the formula (I) where n=4, and a second proportion (y mol %) of the compounds of the formula (I) where n is 2,3,5, or 6, and, based on a 100 mol % total quantity of the compounds of the formula (I)

80 mol %≤(x)≤[100 mol %−(y)].

2. The polysulfide mixture as claimed in claim 1, wherein, for others of the two or more compounds of the formula (I), n is 3, and a proportion of the compounds of the formula (I) where n=3 is less than 10 mol %, of the total quantity of polysulfide compounds of the formula (I).

3. The polysulfide mixture as claimed in claim 1, wherein, for others of the two or more compounds of the formula (I), n is 5, and a proportion of the compounds of the formula (I) where n=5 is less than 10 mol % of the total quantity of polysulfide compounds of the formula (I).

4. The polysulfide mixture as claimed in claim 1, wherein the mixture contains compounds that do not correspond to the formula (I), and a proportion of the compounds which do not correspond to the formula (I) is less than 10 mol %.

5. The polysulfide mixture as claimed in claim 1, wherein each R is methyl.

6. A process for the production of the polysulfide mixture as claimed in claim 1, the process comprising:
contacting alkyl 3-mercaptooropionate and $S_2Cl_2$ in an inert medium, wherein, alkyl is methyl, ethyl, n-propyl, 2-propyl, n-butyl, isobutyl, tert-butyl, or $C_5$-$C_8$ alkyl.

7. The process as claimed in claim 6, wherein:
the inert medium is a first initial amount of the compounds of the formula (I) and the process comprises contacting the alkyl 3-mercaptopropionate and the $S_2Cl_2$ in the inert medium of compounds of the formula (I) to produce a resultant mixture of the first initial amount of compounds of the formula (I) plus an additional amount of reaction products of the compounds of the formula (I);
the contacting of the alkyl 3-mercaptopropionate and the $S_2Cl_2$ in the inert medium takes place at temperatures of 0° C. to 60° C.; and
since the inert medium comprises compounds of the formula (I) and the resultant reaction product are compounds of the formula(I) an additional separtion step of separating the resultant products from the inert medium is not required.

8. The process as claimed in claim 6, wherein HCl gas is produced as a reaction byproduct during the contacting and the method further comprises removing all or some of the resultant HCl gas from the mixture during the reaction via passage of inert gas and/or via application of vacuum.

9. A rubber mixture comprising:
at least one rubber, and
the polysulfide mixture as claimed in claim 1.

10. The rubber mixture as claimed in claim 9, further comprising:
at least one sulfur-containing alkoxysiane, and
at least one silica-based filler.

11. The rubber mixture as claimed in claim 9, further comprising at least one crosslinking agent.

12. The rubber mixture as claimed in claim 9, wherein the at least one rubber comprises at least one SBR rubber and at least one BR rubber, in a ratio by weight of SBR rubber to BR rubber of 60:40 to 90:10.

13. The rubber mixture as claimed in claim 12, further comprising at least one NR rubber, in a ratio by weight of SBR rubber to BR rubber to NR rubber of from 60 to 85:10 to 35:5 to 20.

14. A process for the production of the rubber mixture as claimed in claim 9, the process comprising mixing the at least one rubber and the polysulfide mixture as claimed in claim 1.

15. A process for the production of vulcanizates, the process comprising vulcanizing the rubber mixture as claimed in claim 9 at a temperature of 100 to 200° C.

16. A vulcanizate obtained via vulcanization of the rubber mixture as claimed in claim 9.

17. A rubber product comprising the vulcanizate as claimed in claim 16.

18. A vehicle comprising the rubber product as claimed in claim 17.

19. An additive composition comprising at least one sulfur-containing alkoxysilane and a polysulfide mixture as claimed in claim 1.

20. A method for producing the additive composition as claimed in claim 19, the method comprising combining the polysulfide mixture as claimed in claim 1 with the at least one sulfur-containing alkoxysilane.

21. A process for reducing the roving resistance of tires, the process comprising mixing the polysulfide mixture as claimed in claim 1 with a non-crosslinked or partially crosslinked rubber mixture, forming at least parts of the tire from the rubber mixture, and vulcanizing the mixture.

22. The polysulfide mixture as claimed in claim 1, wherein:
a proportion of compounds where n=4 is at least 85%;
for another of the two or more compounds of the formula (I), n is 4, and a proportion of the compounds of the formula (I) where n=3 is less than 6% based on the total quantity of polysulfide compounds of the formula (I); and
for another of the two or more compounds of the formula (I), n is 5, and a proportion of the compounds of the formula (I) where n=5 is less than 6% based on the total quantity of polysulfide compounds of the formula (I); and
the mixture contains compounds that do not correspond to the formula (I) and a proportion of compounds which do not correspond to the formula (I) is less than 3%.

23. The polysulfide mixture as claimed in claim 1, wherein:
each R is methyl, ethyl, n-propyl, n-butyl, or isooctyl,
a proportion of compounds where n=4 is at least 90%;
for another of the two or more compounds of the formula (I), n is 3, and a proportion of the compounds of the formula (I) where n=3 is less than 4% based on the total quantity of polysulfide compounds of the formula (I); and
for another of the two or more compounds of the formula (I), n is 5, and a proportion of the compounds of the formula (I) where n=5 is less than 4% based on the total quantity of polysulfide compounds of the formula (I);
the mixture contains compounds that do not correspond to the formula (I) and a proportion of compounds which do not correspond to the formula (I) is less than 1%.

24. The polysulficie mixture as claimed in claim 1, wherein:
each R is methyl;
a proportion of compounds where n=4 is 95-99 mol %;
for another of the two or more compounds of the formula (I), n is 3, and a proportion of the compounds of the formula (I) where n=3 is less than 2 mol % based on the total quantity of polysulfide compounds of the formula (I); and
for another of the two or more compounds of the formula (I), n is 5, and a proportion of the compounds of the formula (I) where n=5 is less than 3 mol % based on the total quantity of polysulfide compounds of the formula (I); and
the mixture contains compounds that do not correspond to the formula (I) and a proportion of compounds which do not correspond to the formula (I) is less than 0.2 mol % of compound of the polysulfide mixture.

25. The process as claimed in claim 6, wherein:
the contacting of the alkyl 3-mercaptopropionate and the $S_2Cl_2$ is carried out at a temperature of 10° C. to 45° C. to form the compounds of the formula (I)in inert medium; and
the process comprises removing the inert medium from the compounds of the formula (I) at a temperature no higher than 40° C.

26. The process as claimed in claim 6, wherein:
the contacting of the alkyl 3-mercaptopropionate and $S_2Cl_2$ is carried out at a temperature of 15° C. to 35° C. to form the compounds of the formula (I) in inert medium; and
the process comprises removing the inert medium from the compound of the formula (I) at temperature higher than 35° C.

27. The process as claimed in claim 6, wherein:
the contacting of the alkyl 3-mercaptopropionate and $S_2Cl_2$ is carried out at a temperature of 20°C. to 30C. to form the compound of the formula(I) in inert medium;
the process comprises removing the inert medium from the compound of the formula (I)at a temperature no higher than 30° C.; and
the alkyl 3-mercaptopropionate is methyl 3-mercaptopropionate.

28. The process for the production of vulcanizates as claimed in claim 15, wherein the temperature is 130 to 180° C.

29. The additive composition as claimed in claim 19, wherein the at least one sulfur-containing alkoxysilahe is selected from the group consisting of bis(triethoxysilyipropyl) tetrasulfane, bis(triethoxysilylpropyl) disulfane, 3-(triethoxysilyl)-1-propanethiol, polyether-functionalized meroaptosilane, and thioester-functionalized alkoxysilane.

* * * * *